United States Patent [19]
Johnson

[11] Patent Number: 5,658,252
[45] Date of Patent: Aug. 19, 1997

[54] DRUG PUMP INCLUDING PRESSURE PLATE AND TUBE

[75] Inventor: Jay Gregory Johnson, Maple Plain, Minn.

[73] Assignee: SIMS Deltec, Inc., St. Paul, Minn.

[21] Appl. No.: 585,687

[22] Filed: Jan. 12, 1996

Related U.S. Application Data

[63] Continuation-in-part of Ser. No. 228,508, Apr. 15, 1994, Pat. No. 5,531,697, and Ser. No. 480,519, Jun. 7, 1995, which is a continuation of Ser. No. 156,040, Nov. 22, 1993, abandoned.

[51] Int. Cl.$^6$ .................................................. A61M 37/00
[52] U.S. Cl. .................. 604/131; 604/151; 128/DIG. 12; 128/DIG. 13
[58] Field of Search ........................ 604/151–153, 604/250–254, 65–67, 50, 30, 31–34, 131, 132, 246; 128/DIG. 12, 13

[56] References Cited

U.S. PATENT DOCUMENTS

| | | |
|---|---|---|
| 3,402,673 | 9/1968 | Ballentine et al. . |
| 4,187,057 | 2/1980 | Xanthopoulos . |
| 4,398,908 | 8/1983 | Siposs . |
| 4,482,347 | 11/1984 | Borsanyi . |
| 4,537,561 | 8/1985 | Xanthopoulos . |
| 4,565,542 | 1/1986 | Berg . |
| 4,585,399 | 4/1986 | Baier . |
| 4,657,486 | 4/1987 | Stempfle et al. . |
| 4,671,792 | 6/1987 | Borsanyi . |
| 4,798,590 | 1/1989 | O'Leary et al. . |
| 4,886,431 | 12/1989 | Soderquist et al. . |
| 5,047,014 | 9/1991 | Mosebach et al. . |
| 5,131,816 | 7/1992 | Brown et al. . |
| 5,147,313 | 9/1992 | Dikeman . |
| 5,181,842 | 1/1993 | Sunderland et al. . |
| 5,213,483 | 5/1993 | Flaherty et al. . |
| 5,219,327 | 6/1993 | Okada . |
| 5,336,190 | 8/1994 | Moss et al. . |
| 5,374,251 | 12/1994 | Smith . |
| 5,397,222 | 3/1995 | Moss et al. . |
| 5,425,173 | 6/1995 | Moss et al. . |

*Primary Examiner*—Robert A. Hafer
*Assistant Examiner*—Perry E. Van Over
*Attorney, Agent, or Firm*—Merchant, Gould Smith, Edell Welter & Schmidt P.A.

[57] ABSTRACT

A pressure plate for use with a peristaltic pump having a base with a plurality of ribs attached to one surface of the base, each rib having a bottom surface, a top surface and an angled surface extending at an angle from the bottom to the top surface. Each rib being attached to the base such that the angled surface of each rib is oppositely disposed from the angled surface of another rib so that a channel is formed between each pair of oppositely disposed ribs. A securing mechanism is attached to the pressure plate to secure a compressible tube and an attachment mechanism is provided for attaching a pump mechanism to the pressure plate. One securing mechanism includes two clamps at opposite ends of the pressure plate with spaced apart retaining lips. Adhesive attachment of the tube to the pressure plate is also provided.

11 Claims, 6 Drawing Sheets

DRUG PUMP INCLUDING PRESSURE PLATE AND TUBE

RELATED APPLICATIONS

The present application is a continuation-in-part application of application Ser. No. 08/228,508, filed Apr. 15, 1994 now U.S. Pat. No. 5,531,697, and application Ser. No. 08/480,519, filed Jun. 7, 1995, which is a continuation of application Ser. No. 08/156,040, filed Nov. 22, 1993, now abandoned, the disclosures of which are hereby incorporated by reference.

FIELD OF THE INVENTION

The invention relates generally to drug infusion pumps and more particularly to pressure plates and compressible tubes for use in drug infusion pumps.

BACKGROUND OF THE INVENTION

Figure 1:
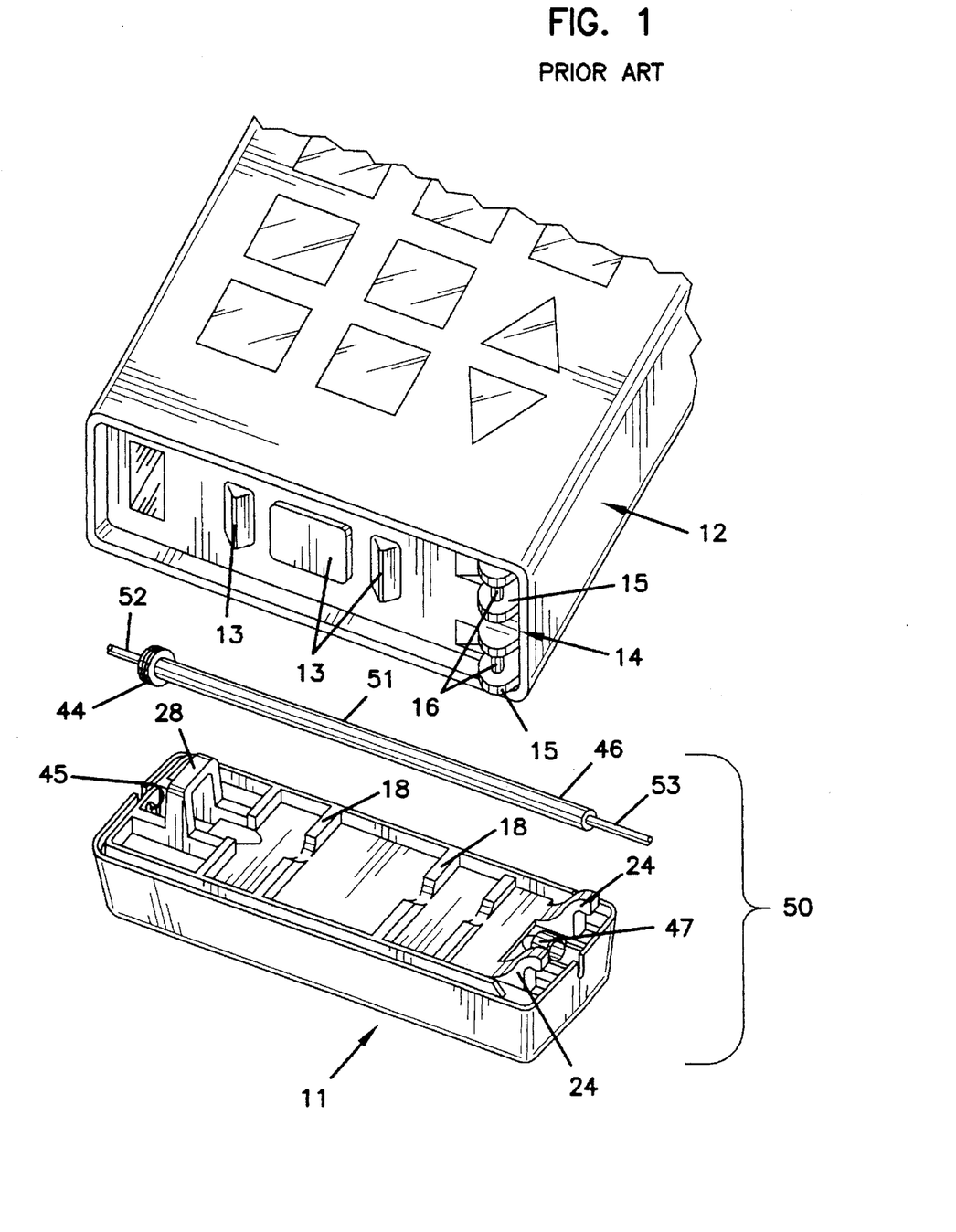
FIG. 1 is a perspective view of a prior art version of a drug infusion pump with portions shown in exploded view.

Currently, drugs or other fluids are often administered to patients intravenously through the use of a drug infusion pump. One commonly used type of drug infusion pump is a linear peristaltic drug infusion pump as shown in FIG. 1. This type of pump typically includes a peristaltic pump mechanism 12 having tube engaging members 13, and a detachable pressure plate 11. Pump mechanism 12 is part of a control module including control circuitry and data input structure, such as a keypad. The main surface of pressure plate 11 contains a plurality of oppositely disposed ribs 18 with a U-shaped channel between the ribs. A compressible tube 46 is attached to pressure plate 11 by threading the tube through an aperture 45 in one end of the pressure plate, through a loop-shaped pump anchor 28 and through a ring 47 at the opposite end of the pressure plate. Tube 46 is secured to pressure plate 11 and positioned in the U-shaped channels by use of ring 47 at one end and a restraint 44 at another end which is force-fit into aperture 45 of pressure plate 11. Together, tube 46 and pressure plate 11 form a tube/pressure plate assembly 50. Tube 46 is adhesively attached to restraint 44 and ring 47.

Tube/pressure plate assembly 50 is then attached to pump mechanism 12 by pump-securing extensions or hooks 24 on pressure plate 11 which engage a suspended pin assembly 14 having support plates 15 and pins 16 which are located on the bottom of pump mechanism 12. Pump anchor 28 located on pressure plate 11 engages a releasable engaging mechanism inside pump mechanism 12 to secure pressure plate 11 to pump mechanism 12. During use, tube engaging members 13 act in a predetermined sequence to draw a predetermined amount of fluid into tube 46 from a fluid reservoir and then expel the predetermined amount of fluid from tube 46 to the patient. The reservoir may be mounted to the pressure plate or it may be remote.

Because the amount of fluid introduced through tube 46 is controlled by the compression of tube 46, tube 46 is loosely fitted onto pressure plate 11 to allow the proper amount of compression to occur. To achieve a loose fit, tube 46 is only attached, such as by adhesive or solvent bond, to pressure plate 11 at opposite ends of pressure plate 11. Unfortunately, because tube 46 is loosely fitted, the tube can occasionally become misaligned with the U-shaped channel during the attachment of pressure plate 11 to pump mechanism 12 by the caregiver or patient. When misalignment occurs, tube 46 can be pinched between one or more of ribs 18 and pump mechanism 12 causing improper compression of tube 46 and a resulting improper delivery of fluids through tube 46. Misalignment may result in free flow, insufficient flow or no flow through tube 46.

As larger tubes are used to increase the amount of fluid flow per pump activation, the problems of misalignment are more likely to occur. The larger tubes will have a greater tendency to bow upward, increasing the chance of being pinched between a rib 18 and pump mechanism 12. Such upward bowing is caused in part by the increased flexibility of the tube and the tube entering and exiting the pressure plate at a vertical height lower than the main surface of the pressure plate.

A current commercial pressure plate 11 with compressible tube 46 by SIMS Deltec, Inc. of St. Paul, Minn., includes a large diameter portion 51, a first small diameter portion 52 attached to one end of large diameter portion 51, and a second small diameter portion 53 attached at the other end of large diameter portion 51. Large diameter portion 51 has an outer diameter of approximately 0.164 inches, while first and second small diameter portions 52, 53 each have an outer diameter of approximately 0.100 inches. Large diameter portion 51 has a wall thickness of approximately 0.032 inches and is capable of delivering approximately 50 microliters per activation of pump mechanism 12. The vertical drop at the ends of pressure plate 11 is about 0.050 inches. In some instances, tube misalignment is a problem for the prior system of FIG. 1.

There is a need in some cases to use tubes 46 with larger outer and inner diameters than the prior system of FIG. 1 to achieve a higher fluid flow. The larger tubes may be more flexible, and therefore more prone to bowing. Further, the larger tubes need to have more vertical drop at the ends of pressure plate 11 to avoid pinching off by pump mechanism 12. This may further increase tube bowing and the likelihood of misalignment.

Therefore, there arises a need for a pump pressure plate for use with a drug infusion pump which will automatically and reliably result in compressible tubes being aligned adjacent the pump mechanism. There is also a need for a more easily assembled pressure plate with compressible tube.

SUMMARY OF THE INVENTION

The present invention is for a pump pressure plate for a pump system where the pressure plate has a main surface and a plurality of ribs attached to the main surface for centering a compressible tube under a pump mechanism with reciprocally moveable tube engaging members. Each rib has a top surface, a bottom surface and an angled surface, the bottom surface of each rib being attached to the main surface such that the angled surface of each rib is oppositely disposed from the angled surface of another rib so that a truncated V-shaped channel is formed between each pair of oppositely disposed ribs. The pressure plate also includes a securing mechanism for securing a compressible tube to the pressure plate, and a mounting mechanism for attaching the pump mechanism to the pressure plate. Other configurations of the ribs are possible to achieve a tube centering effect for loosely fitted tubes that are initially misaligned during attachment of the pressure plates to the pump mechanisms.

One preferred securing mechanism for the tube to the pressure plate includes two clamps at opposite ends of the pressure plate which grip the compressible tube. Adhesive may be added to more securely mount the tube to the pressure plate.

One preferred mounting mechanism for mounting the pressure plate to the pump mechanism includes two hooks and a loop-shaped pump anchor extending from the pressure plate to cooperate with mating structure on the pump mechanism.

The present invention meets the need for a pressure plate which automatically and reliably aligns a compressible tube within the channel between the ribs by the use of ribs having an angled surface that are attached to the pressure plate such that a truncated V-shaped channel, or other tube centering shape, is formed between each pair of ribs. If the compressible tube is out of alignment with the center of the channel during the attachment of the pump mechanism to the pressure plate, the downward force placed on the tube during attachment causes the tube to move down the angled surface and into the bottom of the channel. Therefore, the present invention enables a caregiver or patient to attach the tube/pressure plate assembly to the pump mechanism without fear of misalignment of the tube or additional time and effort to assure alignment of the tube with the channel.

Another advantage of the present invention is that the tube can be easily replaced, if desired, with a second tube through the use of the clamps on the pressure plate. This would allow reuse of the pressure plate, if desired.

A further advantage of the present invention is that no external clamping structures are needed during manufacture since the clamps retain the tube in position on the pressure plate, such as when adhesive is applied to attach the tube to the pressure plate.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, wherein like reference letters and numerals indicate corresponding elements throughout the several views.

DETAILED DESCRIPTION OF THE PREFERRED EMBODIMENTS

The present invention provides structure for centering an initially misaligned compressible tube positioned between a pressure plate and a pump mechanism of a pump system. During mounting of the pressure plate to the pump mechanism, a misaligned tube will be automatically centered adjacent to the tube engaging members of the pump mechanism. The present invention also provides structure permitting selective and automatic hold down of a compressible tube to a pressure plate of a pump system. The hold down of the tube can be advantageously utilized as an adhesive clamp during assembly of a pressure plate with a permanently held tube, or as a temporary clamp during use in the case of a reusable pressure plate where the tube is replaced between uses.

Figure 2:
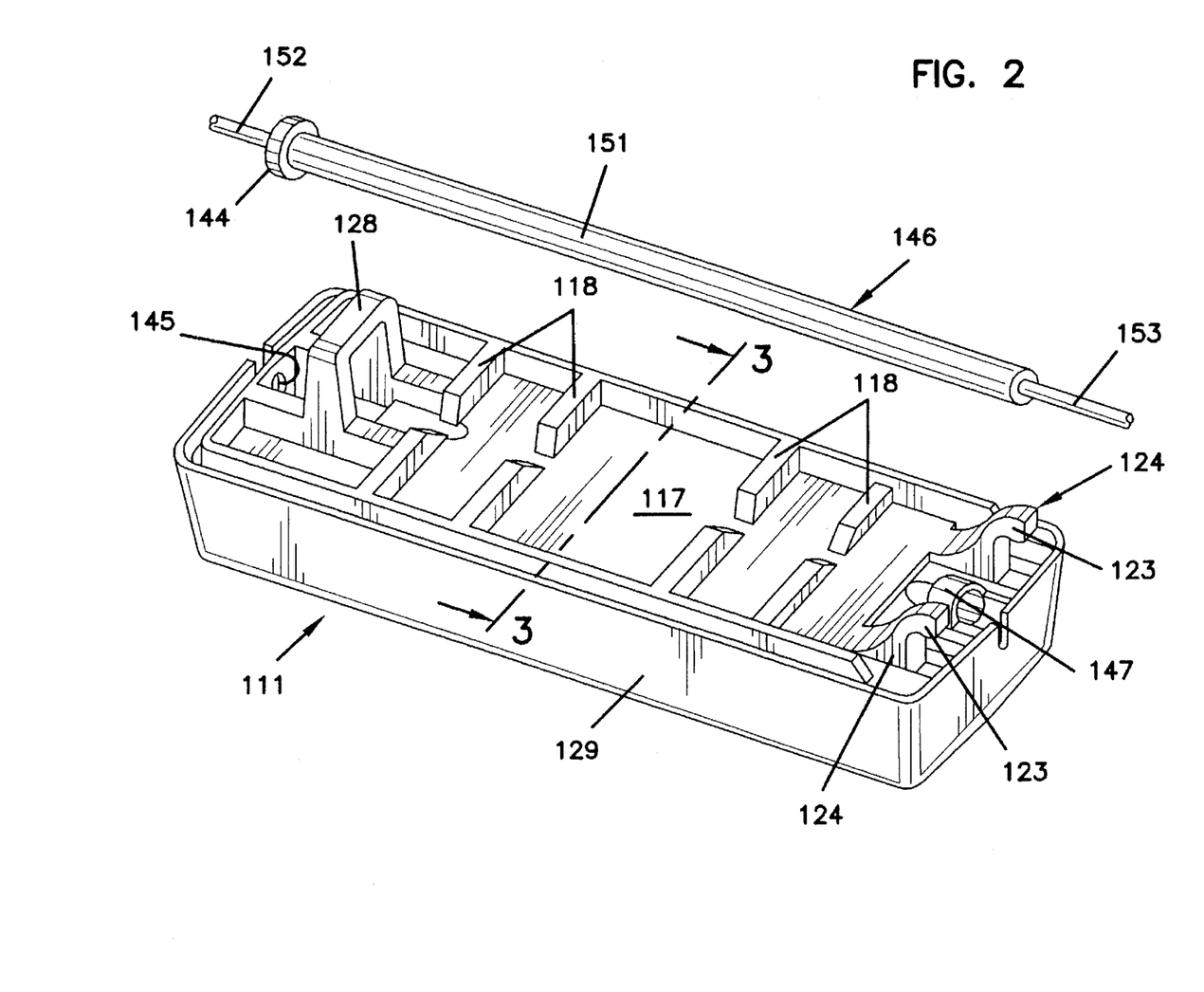
FIG. 2 is an exploded perspective view of a first preferred embodiment of a pressure plate and a tube in accordance with the invention.
Figure 3:
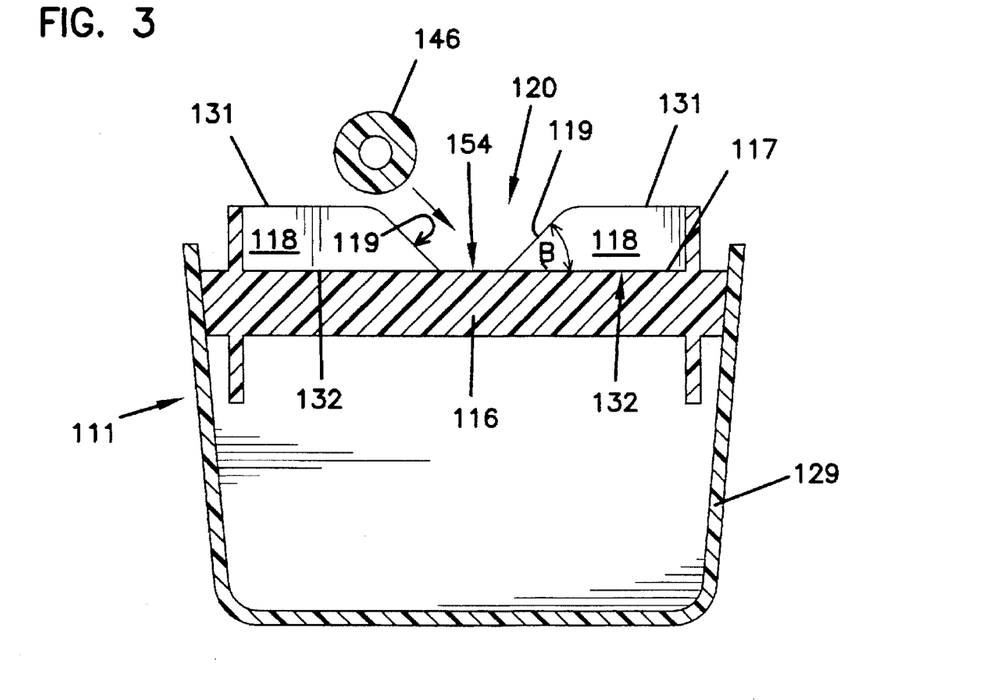
FIG. 3 is a cross-sectional end view of the pressure plate of FIG. 2 as shown along section 3—3 and illustrating the tube initially out of alignment.
Figure 4:
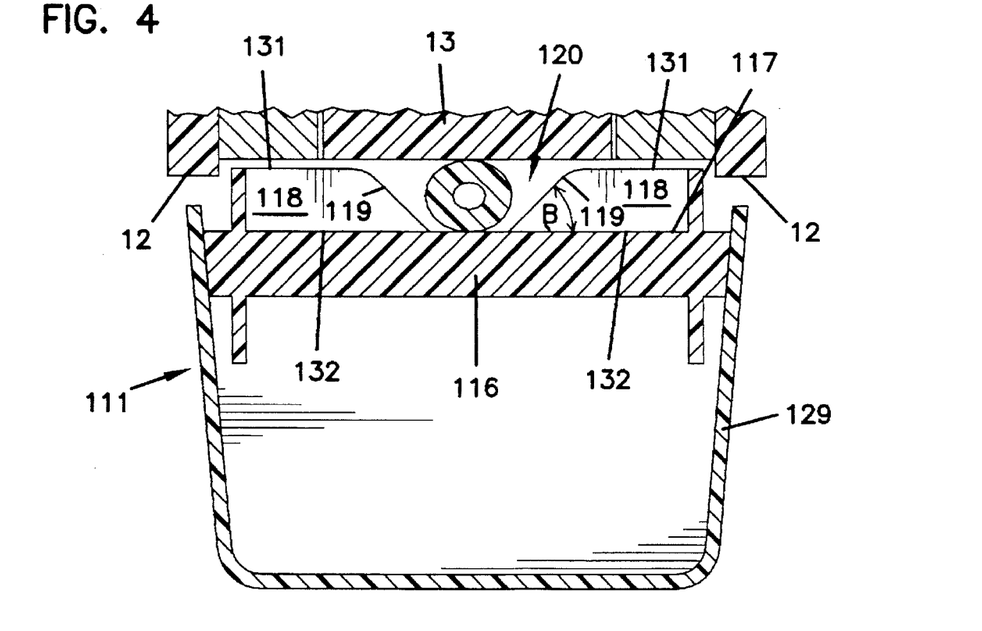
FIG. 4 is a modified view of FIG. 3 showing the tube now in alignment with a channel of the pressure plate, and the pressure plate mounted to a pump mechanism.

Referring now to FIGS. 2–4, a first preferred embodiment of the invention includes a pump pressure plate 111 having a base 116 with a main surface 117 and a plurality of ribs 118 that are attached to main surface 117 of pressure plate 111. Pressure plate 111 is mountable to pump mechanism 12 of FIG. 1.

As shown in FIG. 3, each rib 118 has a top surface 131, a bottom surface 132 and an angled surface 119 such that bottom surface 132 is longer than top surface 131. The intersection between top surface 131 and angled surface 119 is preferably rounded (such as with a radius of one-half of the tube outside diameter) to prevent a compressible tube 146 from catching on any sharp corners during tube centering. Bottom surface 132 of each rib 118 is attached to main surface 117 such that each rib 118 is oppositely disposed from a second rib 118 so that angled surfaces 119 of each pair of oppositely disposed ribs 118 form a truncated V-shaped channel 120 between the oppositely disposed ribs 118. Those skilled in the art will recognize that the lengths of top surface 131 and bottom surface 132 could be varied as long as the angled surfaces were positioned such that a truncated V-shaped channel 120 was formed by angled surfaces 119 and main surface 117. Preferably, pressure plate 111 is made from a molded plastic, such as polycarbonate.

As shown in FIG. 2, compressible tube 146 is securable to pressure plate 111 by a ring 147, a restraint 144 and an aperture 145, as described previously with respect to FIG. 1, for example. Compressible tube 146 preferably is made from a flexible PVC material as commonly used in the industry. Those skilled in the art will recognize that other securing devices could be used with the present invention including expandable clips, snaps, retaining lips or the like in a temporary manner or in a more permanent manner, as desired. Preferably, adhesive, such as UV cured polyurethane, secures tube 142 to pressure plate 111 at each end.

In the first preferred embodiment, compressible tube 146 is comprised of a large diameter portion 151, a first small diameter portion 152 and a second small diameter portion 153. Large diameter portion 151 preferably has length that is sized to extend for the entire length of pressure plate 111 from aperture 145 through ring 147. First small diameter portion 152 is attached to one end of large diameter portion 151 and delivers fluids from a fluid reservoir to large diameter portion 151. Second small diameter portion 153 is attached to the opposite end of large diameter portion 151 and delivers fluids from large diameter portion 151 to the patient. First and second small diameter portions 152, 153 may be at approximately 0.164 inches outer diameter, and 0.032 inch wall thickness, and large diameter portion 151 at approximately 0.228 inches outer diameter with an approximately 0.034 inch wall thickness, for example, to achieve a higher flow during use. Such construction achieves a fluid flow of 125 microliters per activation of pump mechanism 12. By changing the expulsor size of the pump mechanism, or by changing the pressure plate distance from the pump mechanism, other pump volumes can be achieved with tube 146, such as 100 microliters. Other volumes are possible, depending on tube size, expulsor size, and amount of compression of tube 146. Those skilled in the art will recognize that other compressible tube configurations and materials could be used with the present invention.

One preferred manner of attaching pressure plate 111 to pump mechanism 12 is to use a pair of extensions 124 attached to pressure plate 111 to engage suspended pin assembly 14 on the bottom of pump mechanism 12 and a pump anchor 128 attached to main surface 117 for engaging a releasable engaging mechanism located in pump mechanism 12. Each extension 124 would be attached to pressure plate 111 and would have a lip 123 to engage suspended pin assembly 14. Suspended pin assembly 14 is comprised of a plurality of support plates 15 with pins 16 attached therebetween as described for FIG. 1. When attaching pump mechanism 12 to pressure plate 111, lips 123 are inserted above pins 16 in suspended pin assembly 14. Pump mechanism 12 is then rotated downwardly (and/or pressure plate 111 upwardly) thereby securing pins 16 beneath lips 123 on extensions 124 and aligning pump anchor 128 with the releasable engaging mechanism. Once attached, pump mechanism can be activated to move tube engaging members 13 is a predetermined manner to pump fluid to a patient. Examples of pumping mechanisms useable in the pump system are shown in U.S. Pat. Nos. 4,559,038 and 5,364,242, the disclosures of which are incorporated by reference.

As shown in FIGS. 3 and 4, the present invention's use of ribs 118 having angled surfaces 119 to form a truncated V-shaped channel 120 eliminates the alignment problems that may arise from the attachment of pressure plate 111 to pump mechanism 12. If compressible tube 146 should be out of line with the truncated V-shaped channel as shown in FIG. 3, the vertical forces exerted on the compressible tube during assembly are transferred into an angular force by the presence of angled surface 119. The frictional forces are overcome during the assembly operation. Further, compressible tube 146 does not catch on the upper portion of rib 118. Therefore, unlike the prior art, compressible tube 146 is forced into the proper position as shown in FIG. 4.

Truncated V-shaped channel 120 is arranged and configured to assure that compressible tube 146 remains centered within channel 120. Because the distance between pump mechanism 12 and main surface 117 of pressure plate 111 is typically less than the outer diameter of compressible tube 146, compressible tube 146 will be partially compressed even in areas where the tube-engaging members 13 are not located, such as in channel 120. This is especially true for high-flow compressible tube designs. Because compressible tube 146 is partially compressed, a portion of compressible tube 146 will be in contact with main surface 117 of pressure plate 111 (hereinafter referred to as "L"). Those skilled in the art will recognize that L would vary with the diameter of compressible tube 146 and the distance between main surface 117 and pump mechanism 12. If bottom surface 154 of channel 120 between angled surfaces 119 of the oppositely-disposed ribs 118 is greater than L, the compressible tube could move laterally across bottom surface 154 causing a misalignment of compressible tube 146 and possible improper compression by tube-engaging member 13. Therefore, in the preferred embodiment, bottom surface 154 of channel 120 between angled surfaces 119 of the oppositely disposed ribs 118 should be less than or equal to L.

Figure 10:
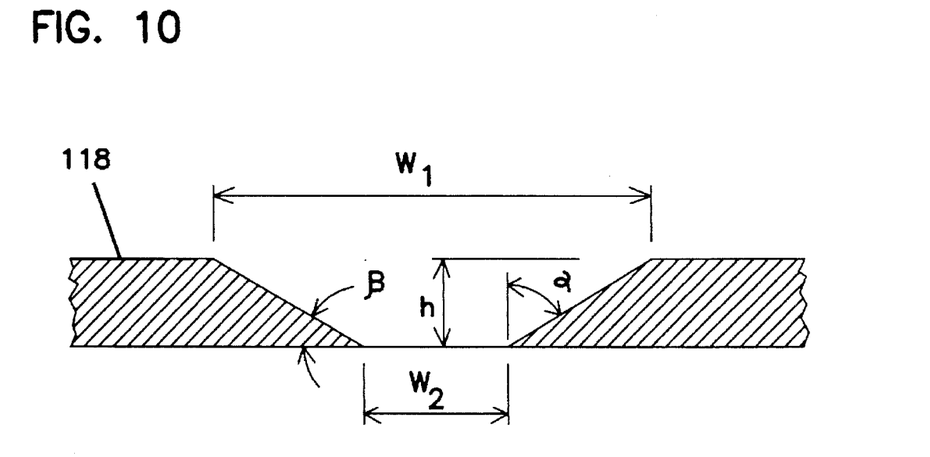
FIGS. 10 and 11 illustrate features of the tube-centering channel configuration.
Figure 11:
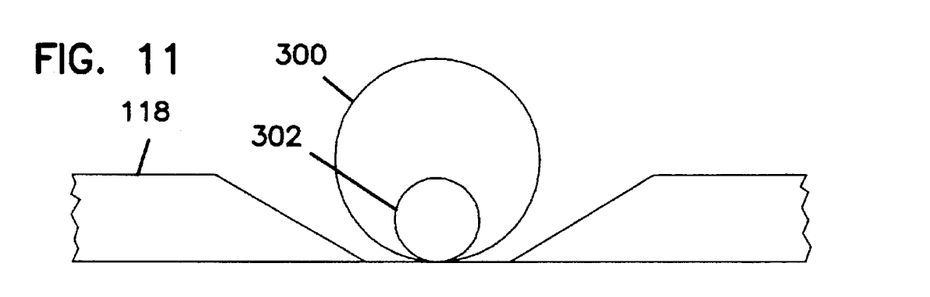

Distance L can be calculated by measuring the distance between the pressure plate and the pump mechanism (standoff height, hereinafter also referred to as "h"), and using that measurement and the tube outside diameter to compute the width of the compressed tube in contact with the pressure plate. In FIG. 10, a preferred maximum of $W_2$ can be calculated from the h dimension and the tube outside diameter dimension. To further maximize the tube centering effect, $W_1$ should be maximized. This allows for more misaligned tubes to be centered than a narrower $W_1$. The opening to channel 120 is $W_1$ and is preferably less than or equal to $W_2$ plus 2 h divided by the coefficient of friction. Therefore, $W_2$ may range from zero to $\Pi/2$ times tube outside diameter minus h. In other words, $W_2$ may range from zero to one-half the difference between the tube circumference and the circumference of a tube with the standoff height as the outside diameter. FIG. 11 shows generally tube 300 prior to attachment to the pump mechanism. Tube 302 of FIG. 11 is a tube generally having an outside diameter equal to the standoff height.

Dimension $W_1$ is less than or equal to the bottom flat $W_2$ plus twice the standoff height divided by the coefficient of friction between the tube and the pressure plate. Therefore, the preferred top width $W_1$ is proportional to the standoff height and inversely proportional to the coefficient of friction.

Figure 12:
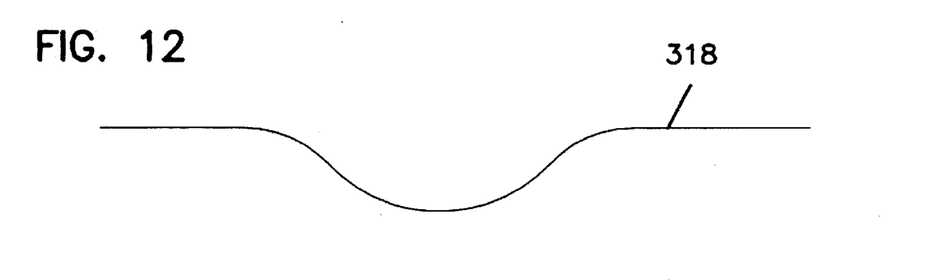
FIGS. 12 and 13 illustrate alternative channel configurations in accordance with the present invention.
Figure 13:
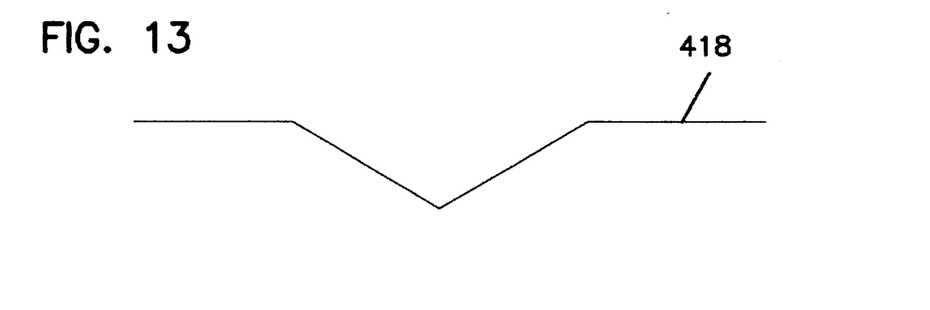

To insure that compressible tube 146 will translate to bottom surface 154 of truncated V-shaped channel 120 during assembly of pressure plate 111 and compressible tube 146 to pump mechanism 12, the angle, generally shown as angle β in FIG. 3, between bottom surface 132 and angled surface 119 of the oppositely-disposed ribs 118 should also be limited in the preferred embodiment. To ensure that compressible tube 146 translates down angled surface 119, the downward force on compressible tube 146 must be greater than the frictional force between compressible tube 146 and angled surface 119. To meet this requirement, angle β must be greater than or equal to 90 degrees minus the arc tangent of 1 divided by the maximum coefficient of static friction, approximately 0.8 in the preferred embodiment. Therefore, angle β must be greater than or equal to 39 degrees in the preferred embodiment. In the case of the preferred embodiment, h is about 0.135 inches, L is about 0.152 inches, and $W_2$ is less than or equal to 0.152 inches. A distance of 0.125 inches works well for $W_2$, and angle β is selected at 40° to allow for proper functioning even if manufactured with slight variations in these features, such as due to customary tolerances of conventional molding operations. Those skilled in the art will recognize that other channel shapes, in addition to the truncated V-shape, could be used as long as bottom surface 154 and angle β meet the above preferred requirements. For example, FIGS. 12 and 13 illustrate alternative configurations of ribs 318 and 418 to ribs 118.

Pressure plate 111 also may have a lower portion 129 attached to base 116. Lower portion 129 of pressure plate 111 is preferably made from an injection-molded rigid material as a separate part, and base 116 with main surface 117, ribs 118, pump anchor 128 and pump securing extensions 124 are injection-molded as a second part. Base 116 is then fastened to lower portion 129 by use of an adhesive, snap arrangement, ultrasonic weld or any other suitable fastening structure. Those skilled in the art will recognize that pressure plate 111 could be made from other materials or made by other methods as long as base 116 of pressure plate 111 is rigid enough to allow tube-engaging members 13 to compress tube 146 between the tube-engaging members 13 and main surface 117.

Tube centering is a balance between several design constraints: (1) avoid catching the tube on any top edge of a centering rib; (2) avoid a shape of the sides of the centering ribs which limits downward translation during centering; (3) properly center the tube in the bottom of the channel between each pair of centering ribs; (4) have the opening to the channel be sufficiently wide to center typical misaligned tubes; and (5) allow for proper engagement and compression of the tube by the tube engaging members when the tube is centered by the ribs, i.e. allow the tube engaging members to close off the tube during use to prevent free flow, or back flow, and allow the tube to appropriately compress and expand to deliver the appropriate volume of fluid per activation. The truncated V-shaped channel 120 with rounded upper corners maximizes the tube centering effect. However, other shapes are possible, such as shown in FIGS. 12 and 13.

Referring now to FIGS. 5–9, a second preferred embodiment of a pressure plate 211 is shown. Pressure plate 211 includes a main surface 217 and a downwardly extending base 226. Extending upwardly from main surface 217 are a pair of hooks 223 adjacent to a first transverse end 222. A loop 228 extends from main surface 217 adjacent to a second transverse end 220. A plurality of rib pairs 218 defining a preferred truncated V-shaped channel as described previously for pressure plate 111 extend from main surface 217 and are spaced apart to receive a compressible tube 249 in a general direction parallel to first and second longitudinal sides 228, 229. Preferably, compressible tube 249 is made of a flexible PVC material as commonly used in the industry like compressible tube 146.

Figure 5:
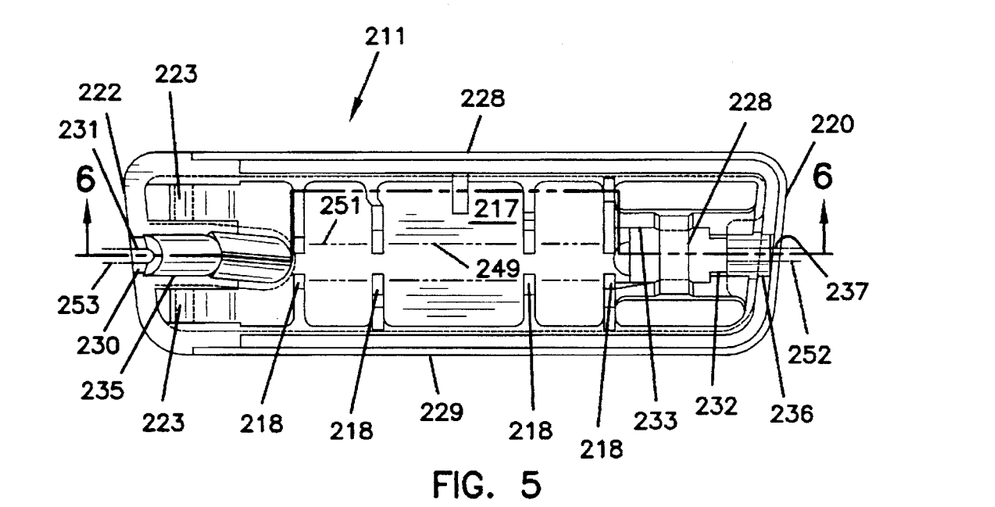
FIG. 5 is a top view of a second preferred embodiment of a pressure plate in accordance with the invention.

In FIG. 5, compressible tube 249 is shown in dashed lines. Compressible tube 249 includes a large diameter portion 251 and two small diameter portions 252, 253 on either end. First and second small diameter portions 252, 253 may be at approximately 0.164 inches outer diameter with an approximately 0.032 inch wall thickness, and large diameter portion 251 at approximately 0.228 inches outer diameter with an approximately 0.034 inch wall thickness. Pump volumes of 125 and 100 microliters or other are possible. FIGS. 5–9 also illustrate an integral construction between main surface 217 and base 226 where the parts are integrally molded. Base 226 generally defines a hollow bottom.

Pressure plate 211 includes clamp features for releasably securing compressible tube 249 to provide a mechanical hold down of compressible tube 249 to pressure plate 211. Such is useful during adhesive attachment or solvent bonding of compressible tube 249 to pressure plate 211 during manufacture to achieve a permanent mount. In particular, first clamp 230 and second clamp 232 provide a hold down of compressible tube 249 to pressure plate 211 on each end of compressible tube 249. First clamp 230 and second clamp 232 hold the compressible tube in place during assembly, allowing an adhesive to set up to bond compressible tube 249 to pressure plate 211 without the need for special extra clamps or external fixtures. Compressible tube 249 snaps into place and is gripped by the clamps. This allows the bonding agent to cure without external hold down structures. Also, the clamps allow for easy manufacture since compressible tube 249 does not have to be threaded through any ring or aperture in pressure plate 211 other than loop 228. A gap in loop 228 may be provided to eliminate the threading operation.

First clamp 230 and second clamp 232 hold the compressible tube in place such that a reusable pressure plate 211 and replaceable tube system results when the tube is not adhesively attached or otherwise permanently attached to the pressure plate.

First clamp 230 includes an angled surface 231 for receiving small diameter portion 253 of compressible tube 249. Angled surface 231 also defines opposed retaining lips 231a, 231b for resiliently gripping and holding compressible tube 249. Retaining lips 231a and 231b are spaced apart at 0.125 inches in the preferred embodiment to hold small diameter portion 253. Larger angled surface 235 provides a convenient surface for adhesive attachment of large diameter portion 251 of compressible tube 249 at end 222 of pressure plate 211. Downward angling of these surfaces helps reduce some of the tube bowing problem. However, the size of the tube still results in tube bowing, where tube centering is desired.

Second clamp 232 defines opposed retaining lips 232a, 232b for resiliently gripping and holding large diameter portion 251 of compressible tube 249. Retaining lips 232a and 232b are spaced apart at 0.200 inches in the preferred embodiment. Surface 236 provides a convenient surface for adhesive attachment of large diameter portion 251 of compressible tube 249 at end 220 of pressure plate 211. Small channel 237 receives small diameter portion 252 of compressible tube 249, during use.

Other tube securing structures are useable with pressure plate 211 instead or one or both of clamps 231 and 232, such as the structures described in application Ser. No. 08/480, 519, filed Jun. 7, 1995, previously incorporated by reference.

Figure 6:
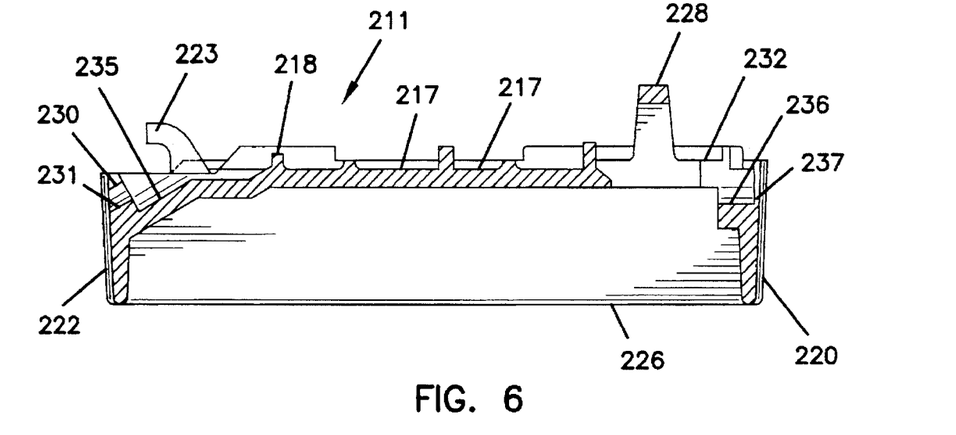
FIG. 6 is a cross-sectional side view of the pressure plate of FIG. 5 as shown along section 6—6.
Figure 7:
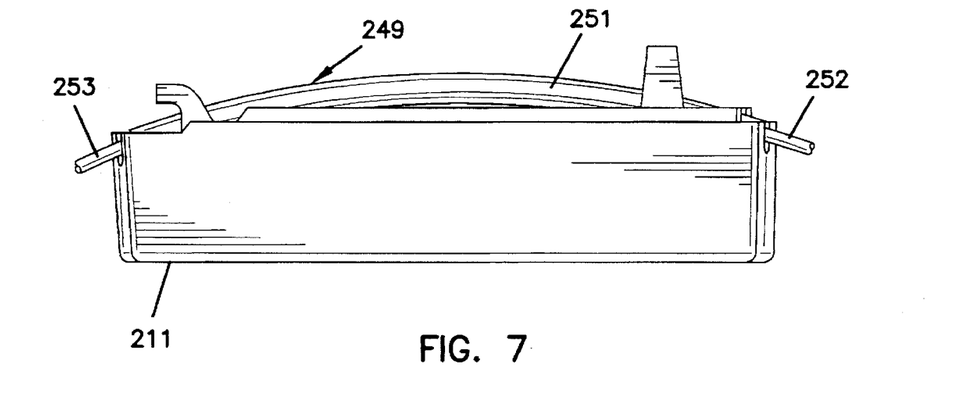
FIG. 7 is a side view of the pressure plate of FIG. 5 showing a tube mounted thereto.
Figure 8:
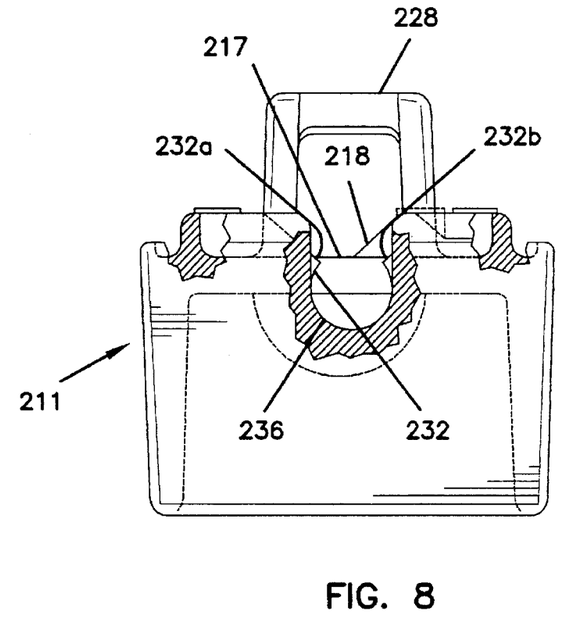
FIG. 8 is an enlarged right end view of the pressure plate of FIG. 5, in partial cross-section.
Figure 9:
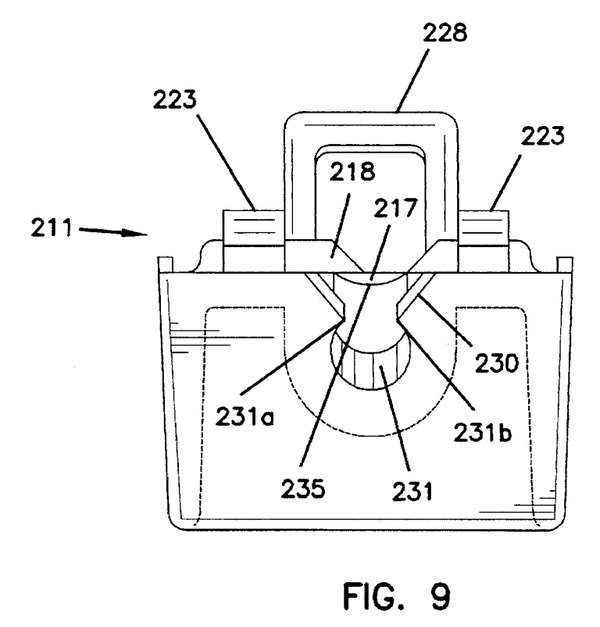
FIG. 9 is an enlarged left end view of the pressure plate of FIG. 5.

Tube bowing or arching as shown in FIG. 7 is due to compressible tube 249 needing to enter and exit pressure plate 211 below the main surface of the pressure plate to avoid pinching compressible tube 249 by pump mechanism 12. For compressible tube 249 shown, a vertical drop of approximately 0.150 inches is desirable. As shown in FIGS. 6, 8 and 9, pressure plate 211 provides for entry and exit of compressible tube 249 to be below the level of main surface 217. Such construction prevents pinching of compressible tube 249 at either end by the pump mechanism. However, tube bowing results, as illustrated in FIG. 7. Such tube bowing increases the need for appropriate tube centering features as noted above.

If an inlet or upstream occlusion sensor is provided, it may be necessary to provide a sufficient restriction in the upstream fluid flow to enable proper functioning of the occlusion sensor. Specifically, this may be the case if the inlet occlusion sensor relies upon a localized vacuum to detect inlet occlusions. For example, the inlet occlusion sensor may be a strain-type beam sensor that records the pump tube force upstream of the pumping mechanism. During a normal pumping cycle, the expulsor rises allowing the pump to fill. During the filling process, the inlet occlusion sensor detects the localized upstream vacuum associated with the fluid rushing to fill the pump tube. This upstream vacuum is present only if there exists a sufficient restriction in the upstream tube inner diameter. This vacuum is temporary; and, as the pump tube fills, the vacuum dissipates. This signal verifies that flow occurs with each pump cycle. During an inlet occlusion, the vacuum does not dissipate. The tube eventually collapses and no contact exists between the pump tube and the inlet occlusion sensor. In that case, the signal would go flat and the occlusion (lack of flow) is identified.

In the case of high flow tubing as described above, it may be advantageous to provide sufficient flow restriction to enable proper functioning of the inlet occlusion sensor. In the above preferred embodiments, the inlet tube inner diameter is noted at approximately 0.100 inches. In the pump described above, if this pump tube size continued unchanged all the way to a remote reservoir, little restriction would exist, and no vacuum (or negative pressure spike) may be detected improved performance may be found if the tube inner diameter is changed from 0.100 inches to about 0.060 inches or less. A restriction which is too small may result in the tube insufficiently filling during the pumping cycle. It is believed that tube inner diameters between about 0.060 inches and about 0.040 inches are appropriate in the above noted embodiments for creating a sufficient negative pressure spike for use in an upstream occlusion sensor system. The reduced diameter portion can extend all the way from the pressure plate to the remote reservoir. Alternatively, a valve or other restriction could be placed in the line, or the bag spike could have a localized small inner diameter so as to produce similar restricted flow results. The amount of tube restriction may vary as fluid flow changes for different tube sizes, different expulsor sizes, and different amounts of tube compression.

Although characteristics and advantages, together with details for structure, materials, function and process steps, have been described in reference to a preferred embodiment herein, it is understood that the disclosure is illustrative. To that degree, various changes made, especially to matters of shape, size and arrangement, to the full extent extended by the general meaning of the terms in which the appended claims are expressed, are within the principles of the present invention.

What is claimed is:

1. A pressure plate for a pump comprising:
   (a) a base having a main surface; and
   (b) a plurality of ribs having a top surface, a bottom surface and an angled surface between the top surface and bottom surface forming an angle between the bottom surface and angled surface, the bottom surface of each rib being attached to the main surface of the base such that the angled surface of each rib is oppositely disposed from the angled surface of another rib so that a truncated V-shaped channel is formed between each pair of oppositely disposed ribs.

2. A pressure plate according to claim 1, further comprising:
   (a) securing means for securing a compressible tube to the pressure plate; and
   (b) attachment means for attaching a pump mechanism to the pressure plate.

3. A pump pressure plate according to claim 1, wherein the distance between the angled surfaces adjacent to the bottom surface of each pair of oppositely disposed ribs is less than or equal to the width of a predetermined compressible tube compressed between the pressure plate and a pump mechanism that is attached to the pressure plate.

4. A pump pressure plate according to claim 1, further comprising a compressible tube secured to the pressure plate.

5. A pump pressure plate according to claim 4, wherein the compressible tube has a large diameter portion with first and second ends that is arranged and configured to be positioned in the truncated V-shaped channels, a first small diameter portion attached to the first end of the large diameter portion for delivering fluids to the large diameter portion, and a second small diameter portion attached to the second end of the large diameter portion for delivering fluids from the large diameter portion to a patient.

6. A pump pressure plate according to claim 5, wherein the large diameter portion has an inner diameter of about 0.160 inches, and the first small diameter portion has an inner diameter of about 0.060 inches or less, and the tube delivers about 100 microliters per activation.

7. A pump pressure plate according to claim 1, wherein the angle between the angled surface and the bottom surface is about 40 degrees.

8. A pump pressure plate according to claim 1, further comprising a pair of clamps mounted to the base at opposite ends of the base, the clamps sized to hold a compressible tube, each clamp having two spaced apart retaining lips.

9. A pump pressure plate according to claim 1, further comprising a pump mechanism mounted to the pressure plate, and a compressible tube positioned in the truncated V-shaped channel and between the pump mechanism and the main surface of the pressure plate.

10. A pump pressure plate for a pump comprising:
    (a) a base having a main surface;
    (b) a plurality of rib pairs mounted to the main surface of the base and defining a channel between each rib pair for receipt of a compressible tube;
    (c) two spaced-apart clamps mounted to the base and sized to resiliently grip the compressible tube; and
    (d) a compressible tube positioned in the channel defined by the rib pairs and resiliently gripped by the clamps, the tube further being adhesively mounted to the base.

11. A pump pressure plate according to claim 10, wherein the rib pairs define a truncated V-shaped channel.

* * * * *